United States Patent
Kim et al.

(10) Patent No.: US 10,058,397 B2
(45) Date of Patent: Aug. 28, 2018

(54) DEVICES, SYSTEMS, AND METHODS FOR CONTAINING INTERNAL BODY PARTS DURING INSERTION INTO THE BODY

(75) Inventors: Sunghoon Kim, Oakland, CA (US); Olajire Idowu, Oakland, CA (US)

(73) Assignee: Children's Hospital & Research Center at Oakland, Oakland, CA (US)

( * ) Notice: Subject to any disclaimer, the term of this patent is extended or adjusted under 35 U.S.C. 154(b) by 625 days.

(21) Appl. No.: 13/364,882

(22) Filed: Feb. 2, 2012

(65) Prior Publication Data
US 2012/0209060 A1   Aug. 16, 2012

Related U.S. Application Data

(60) Provisional application No. 61/442,139, filed on Feb. 11, 2011.

(51) Int. Cl.
| | | |
|---|---|---|
| A61F 2/00 | (2006.01) | |
| A61B 90/40 | (2016.01) | |
| A61B 17/00 | (2006.01) | |
| B65D 33/25 | (2006.01) | |

(52) U.S. Cl.
CPC .... *A61B 90/40* (2016.02); *A61B 2017/00287* (2013.01); *B65D 33/2566* (2013.01)

(58) Field of Classification Search
CPC  B65D 31/12; B65D 33/2566; B65D 81/3266; A61B 90/40
USPC ............... 600/37; 604/87; 606/114; 383/107
See application file for complete search history.

(56) References Cited

U.S. PATENT DOCUMENTS

| | | | |
|---|---|---|---|
| 4,637,061 A * | 1/1987 | Riese | 383/38 |
| 6,467,956 B1 * | 10/2002 | Tilman et al. | 383/61.3 |
| 6,467,959 B1 | 10/2002 | Bircann | |
| 8,613,547 B2 * | 12/2013 | Steele | B31B 19/84 383/10 |
| 9,398,871 B2 | 7/2016 | Idowu et al. | |
| 2004/0158261 A1 * | 8/2004 | Vu | A61B 17/00234 606/114 |
| 2011/0028924 A1 * | 2/2011 | Murray | A61F 5/4407 604/332 |

(Continued)

FOREIGN PATENT DOCUMENTS

RU    2157662 C2 * 10/2000

OTHER PUBLICATIONS

Fischer, James D., et al., Gastroschisis: A Simple Technique for Staged Silo Closure, Aug. 1995, Journal of Pediatric Surgery, vol. 30, No. 8, pp. 1169-1171.*

(Continued)

*Primary Examiner* — Charles A Marmor, II
*Assistant Examiner* — Shannon McBride
(74) *Attorney, Agent, or Firm* — Michael B. Rubin; Bozicevic, Field & Francis LLP

(57) ABSTRACT

Devices for containing exposed internal body parts during insertion into the body of a human or veterinary patient are provided. The devices include a surgical pouch for containing the exposed internal body parts. The devices also include one or more sealing elements disposed on the surgical pouch between the proximal end and the distal end of the surgical pouch such that a section of the pouch is closed off when each sealing element is sealed. Also provided are methods for containing exposed internal body parts of a human or veterinary patient during insertion into the body of the patient.

27 Claims, 5 Drawing Sheets

(56) References Cited

U.S. PATENT DOCUMENTS

2012/0209060 A1    8/2012   Kim et al.
2013/0019374 A1    1/2013   Schwartz
2013/0211378 A1    8/2013   Miller

OTHER PUBLICATIONS

Kidd, J.N., et al., Staged reduction of gastroschisis: a simple method, Mar. 2001, Pediatric Surgery International, vol. 17, pp. 242-244.*

Dabbas, Natalie, et al., GABBY: An ex vivo model for learning and refining the technique fo preformed silo application in the management of gastroschisis, Jul.-Dec. 2009, African Journal of Paediatric Surgery, vol. 6, Issue 2, pp. 73-76.*

Corbitt et al., "Parents' Resource Guide: Gastroschisis" Nationwide Children's Hospital Brochure, 2008.

Kim, Sunghoon, et al.: "Use of pulse oximeter placed on a gastroschisis silo to monitor intestinal oxygen saturation": Pediatr Surg Int, 22: (2006): pp. 763-765.

Othersen and Smith, (1986) "Pneumatic Reduction Bag for Treatment of Gastroschisis and Omphalocele", Ann. Surg., 203(5): pp. 512-515.

\* cited by examiner

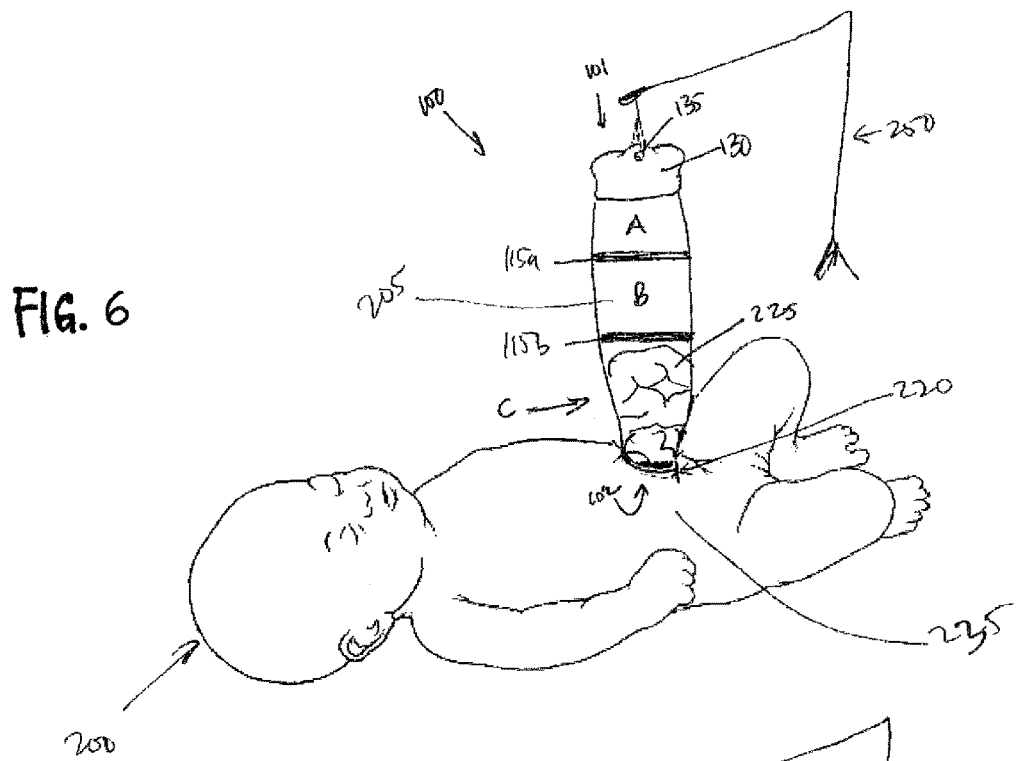

US 10,058,397 B2

DEVICES, SYSTEMS, AND METHODS FOR CONTAINING INTERNAL BODY PARTS DURING INSERTION INTO THE BODY

CROSS-REFERENCES TO RELATED APPLICATIONS

This application claims the benefit of priority under 35 U.S.C. § 119(e) to U.S. Provisional Application No. 61/442,139 filed Feb. 11, 2011, the disclosure of which is incorporated by reference herein in its entirety.

INTRODUCTION

Physicians may be presented with a human or veterinary patient that has exposed internal body parts protruding outside the body. These internal body parts must be put back in the patient during treatment. One example situation where this occurs is with Gastrochisis. Gastroschisis (also called paraomphalocele, laparoschisis, abdominoschisis, or abdominal hernia) is a type of inherited congenital abdominal wall defect in which the intestines and sometimes other organs develop outside the fetal abdomen through an opening in the abdominal wall near the site of the umbilicus. In Gastroschisis, the abdominal wall does not close properly and the stomach, small bowel, and/or large intestine may have come through the small opening near the umbilical cord. Within the womb, these internal body parts are floating free within the amniotic fluid and may not typically present any harm to the baby; however, once born, the baby will require immediate attention.

Surgical pouches, such as sterile plastic or silicone bags, often referred to as "silo" bags, are placed around the exposed internal body parts and used to contain the exposed internal body parts so that they may be shielded from trauma, infection, and dehydration until the body parts are put back within the body. Often the exposed internal body parts may be swollen and inflamed and require time before the swelling and inflammation subside to permit the internal body parts to be safely put back within the body. Insertion of the exposed internal body parts often takes about a week to occur.

For example, the surgical pouch may be suspended above the abdomen during the insertion process. Insertion may include assistance from gravity and/or assistance from the physician (e.g., the physician gently pushes part of the internal body parts back into the body opening). For example, as the swelling goes down and the abdomen has become used to the presence of more internal body parts, portions of the exposed internal body parts may be inserted within the body.

SUMMARY

Devices for containing exposed internal body parts during insertion into the body are provided. The devices include a surgical pouch for containing the exposed internal body parts. The devices also include one or more sealing elements disposed on the surgical pouch between the proximal end and the distal end of the surgical pouch such that a section of the pouch is closed off when each sealing element is sealed. Also provided are methods for containing exposed internal body parts of a human or veterinary patient during insertion into the body of the patient.

BRIEF DESCRIPTION OF THE FIGURES

FIG. 6 illustrates a perspective view of the device shown in FIG. 4 after some exposed internal body parts have been inserted within the patient and a second sealing element sealed, according to some embodiments.

FIG. 7 illustrates a perspective view of the device shown in FIG. 4 after all of the exposed internal body parts have been inserted within the patient, according to some embodiments.

DETAILED DESCRIPTION

Devices

Figure 1:
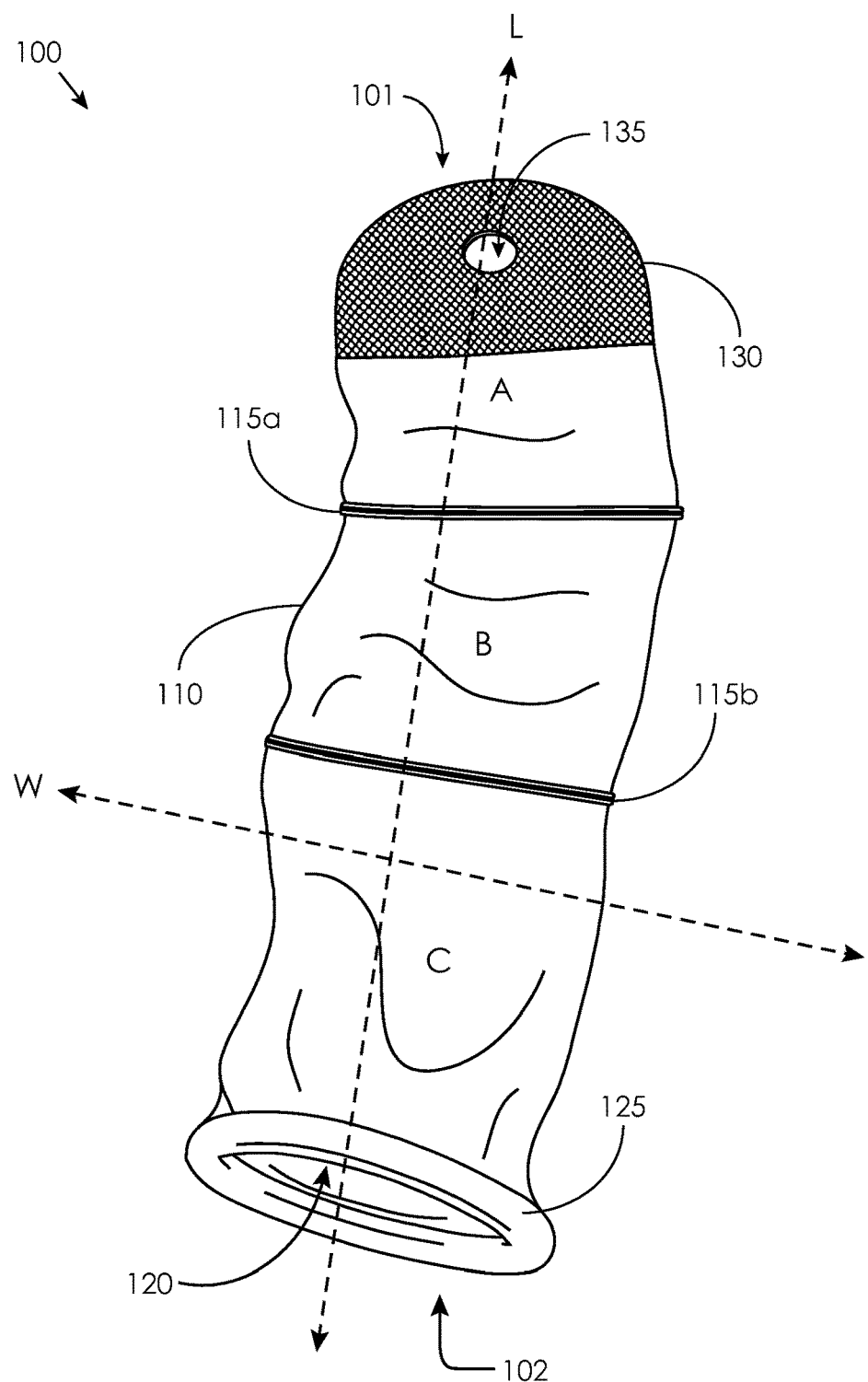
FIG. 1 illustrates a perspective view of a device for containing exposed internal body parts during insertion into the body, according to some embodiments.

Aspects of the present disclosure include devices for containing exposed internal body parts during insertion into the body of a human or veterinary patient. The devices include a surgical pouch for containing the exposed internal body parts. The devices also include one or more sealing elements disposed on the surgical pouch between the proximal end and the distal end of the surgical pouch such that the internal volume of the pouch is decreased when the sealing element is sealed.

The surgical pouch includes a distal end and a proximal end. The term "proximal end", as used herein, refers to the end of the device, surgical pouch, component or member thereof, etc., that is nearest to the patient during use. The term "distal end", as used herein, refers to the end of the device, surgical pouch, component or member thereof, etc., that is farthest from the patient during use. For example, the distal end of the pouch is the end of the pouch that is closest to the distal end of the device. Likewise, the proximal end of the pouch is the end of the pouch that is the closest to the proximal end of the device. The term "longitudinal axis" is also used herein to refer to the axis that extends between the proximal end and distal end of the device. It should be appreciated that the distal end of a component of the device is the end of the component that is closest to the distal end of the device.

The surgical pouch includes a sealing element disposed on the surgical pouch. The sealing element is disposed on the pouch between the distal end and the proximal end of the surgical pouch. The proximal end of the surgical pouch may include, for example, an opening to the pouch. The exposed internal body parts protrude out of the opening in the body (e.g., abdomen) of the patient and may enter the surgical pouch through the opening of the pouch.

When the sealing element is sealed, an empty section of the pouch that does not contain exposed internal body parts is closed off. In some embodiments, more than one sealing element is disposed on the pouch at different locations along the longitudinal axis of the pouch. Each sealing element enables an empty section of the pouch to be closed off from a section of the pouch that contains the exposed internal body parts. Therefore, as more and more of the exposed internal body parts is inserted into the body of the patient, thus taking up less space in the pouch, more and more empty sections of the pouch may be closed off.

When the sealing element is sealed, the internal volume of the section of the pouch containing the body parts is decreased. Each sealing element may be sealed to provide a different internal volume within the pouch. The sealing elements closer to the proximal end provide for a smaller internal volume for that section of the pouch than the sealing elements closer to the distal end of the pouch. Thus, the volume of the section of the surgical pouch containing the body parts is reduced in steps as each sealing element is sealed from the distal end to the proximal end of the pouch.

While any number of sealing elements may be implemented, example numbers of sealing elements may range from, for example, one to fifteen sealing elements, such as two to ten sealing elements, including four to seven sealing elements. The rate at which the internal body parts are displaced into the abdomen may vary. Typical rates in which the internal body parts are displaced when pushed down may be about 1-2 cm per day, for example, with five to seven days to displace the internal body parts all the way into the abdomen. The device may include a single sealing element that can be sealed after each day, for instance. This may require, for example, five or six reductions. The sealing elements may in some cases be spaced approximately 1.5 cm to 2 cm apart. It should be appreciated that the spacing may vary above 2 cm or below 1.5 cm in other embodiments. Furthermore, it should be appreciated that the displacement rate provided is exemplary and that displacement rates may vary under different circumstances.

Any variety of sealing elements may be implemented. For instance, the sealing element may comprise a pair of elements that can be mated together and stay connected so as to close off the corresponding portion of the pouch. Example sealing elements may include fasteners, such as interlocking fasteners (e.g., interlocking fasteners by Ziploc®) with or without a sliding clasp; elements that snap-fit together; elements having hook and loop design; etc. In some embodiments, the one or more sealing elements are interlocking fasteners. It should be appreciated that the same type of sealing element for multiple sealing elements on the same pouch is not necessarily required, and that in other instances, different types of sealing elements may be implemented on the same surgical pouch.

In some embodiments, the sealing element provides an airtight seal that prevents air from passing when the sealing element is sealed. For example, the surgical pouch may include an interlocking fastener that does not permit air to pass when sealed. It should be appreciated that in other embodiments, the sealing element does not necessarily provide an airtight seal that prevents air from passing, but rather generally closes off the empty section of the surgical pouch to enable the pouch to fit closer around the exposed internal body parts than the original entire volume of the surgical pouch.

In some embodiments, the surgical pouch includes a securing element disposed on the surgical pouch near the opening of the surgical pouch. The securing element secures the surgical pouch to the patient. For example, the securing element may be disposed around the opening of the surgical pouch and capable of collapsing for insertion into the opening of the body of the patient and capable of returning to an uncollapsed state once inserted into the opening. For instance, the securing element may be made from a spring or other resilient material or structure. As another example, the securing element may be adhesive disposed around the opening of the surgical pouch to secure the opening around the opening in the body of the patient.

The opening may vary in shape—e.g., circular, elliptical, square, polygonal, or other regular or irregular shape. The securing element may also vary in shape—e.g., circular, elliptical, square, polygonal, or other regular or irregular shape. In some embodiments, the opening is circular and the securing element is a ring positioned around the perimeter of the pouch opening. The ring may be collapsible, for instance, and inserted into the opening while it is collapsed. The ring may also be resilient, for instance, and return to an uncollapsed state when inserted into the body so that it is secured behind the inner wall of the body near the opening in the body. This minimizes the likelihood that the opening of the device becomes detached from the patient. For example, in some embodiments, the ring may comprise a polymeric material that is resilient in nature. In some instances, the ring may further include a spring or spring-like structure made from metal, metal alloys, polymers, etc.

To remove the securing element, an operator (e.g., a physician, physicians assistant, etc.) may reach in and collapse the securing element so that it may be pulled back out of the opening in the body. It should also be appreciated that the securing element may be removed from the body opening by gently pulling on the surgical pouch with enough force to cause the securing element to collapse under pressure from the internal wall of the body at the body opening. The ease by which the securing element may be collapsed under such pressure will depend on how flexible, or how easily collapsible, the securing element is.

The surgical pouch may include various shapes. In some embodiments, the surgical pouch has a shape that is generally longer along the longitudinal axis than along the latitudinal axis. In some instances, the shape of the surgical pouch may be cylindrical or somewhat cylindrical. For example, the opening at the proximal end of the pouch may be circular and the body of the surgical pouch cylindrically extending from the circular opening. In some instances, the distal end of the surgical pouch is closed. For example, the distal end of the surgical pouch may be circular shaped. In other instances, a seam may be provided at the distal end of the surgical pouch that closes off the pouch along a line in the direction of the latitudinal axis.

In some embodiments, the surgical pouch includes a coupling element disposed on the distal end of the device that enables the device to removably couple to a structure so that it may hang above the body opening of the patient. The distal end of the pouch may hang above the proximal end of the pouch, causing the exposed internal body parts in the pouch to be displaced toward the proximal end of the pouch with the opening.

In some instances, the coupling element may comprise a layer of material having a hole within it that enables it to hang from a rod, hook, bar, etc., of an external structure, for example. The layer of material may also serve to reinforce the distal end of the pouch so that it may hang without ripping, tearing, or otherwise becoming damaged, and also serve to provide a seam that close off the distal end of the surgical pouch. The coupling element may comprise any variety of elements for various coupling mechanisms, such as clamps, hooks, hinges, adhesive, strings for tying, hooks, loops, snap-fit elements (e.g., buttons, etc.), etc.

In some embodiments, a seam may be provided along the two sides of the surgical pouch along the longitudinal axis. The seams, for example, may affect the shape of the cross section of the pouch when viewed from a line dividing the proximal end and distal end. The cross section may include, for example, the general shape of a circle, ellipse, or Vesica piscis, depending on the seam and/or shape of the proximal and distal end of the pouch. In some embodiments, where the shape of the above-described cross section is generally a Viseca piscis, certain sealing elements such as interlocking fasteners, for example, may be more easily sealed.

The surgical pouch should be large enough to fit the exposed internal body parts. While it is appreciated that there is no upper limit to the length of the surgical pouch, example lengths of the surgical pouch in Gastrochisis applications, for instance, may range from 6 inches to 30 inches, including 8 inches to 20 inches, such as 10 inches to 18 inches. It should also be appreciated that there is no upper limit to the width of the surgical pouch; however, example widths of the surgical pouch in Gastrochisis applications, for instance, may range from 1 inch to 6 inches, including 1.5 inches to 4.5 inches, such as 2 inches to 4 inches.

The opening in the pouch may vary in size, but should be large enough for the exposed internal body parts to fit through. Example opening sizes may range from 1 inch to 4 inches, such as 1.5 inches to 2.5 inches, including approximately 2 inches. In embodiments where the securing element is disposed around the opening, the size of the securing element may be, for example, approximately the size of the opening.

In use, the surgical pouch is placed around the exposed internal body parts of the patient. For example, the exposed internal body parts may be inserted into the opening of the surgical pouch by the operator (e.g., a physician or other medical personnel). In some instances, the opening may be stretchable or otherwise able to be widened to assist in the insertion of the exposed internal body parts into the surgical pouch.

After the exposed internal body parts are within the surgical pouch, the opening of the surgical pouch is secured to the patient. For example, the proximal end of the surgical pouch may include a securing element that is a collapsible structure that may be collapsed by the operator and inserted into the opening in the body of the patient. Once inside, the collapsible structure returns to its uncollapsed state and secures behind the internal wall of the body. In other embodiments, the opening may include adhesive sealing elements which enable the opening to be adhered to the body of the patient around the opening in the body.

In some instances, the distal end of the surgical pouch is raised up above the body opening. The surgical pouch may include, for example, a coupling element that couples the distal end of the surgical pouch to an external structure so that the distal end of the surgical pouch may be positioned above the proximal end. In such instances, gravity assists to displace the exposed internal body parts toward the proximal end of the surgical pouch—i.e., towards the opening of the surgical pouch.

In some instances, the exposed internal body parts do not fill the entire internal volume of the surgical pouch. As a result, when the body parts are displaced towards the proximal end of the pouch, the distal end of the pouch will include empty space. If the empty space at the distal end of the surgical pouch continues past a sealing element, then that sealing element may be sealed to seal off the empty section of the pouch. For example, the operator may slide an interlocking fastener to seal off the empty section of the pouch. If more than one sealing element is implemented and the empty space continues past multiple sealing elements, then each of those sealing elements may be sealed to close off a corresponding empty section of the pouch. It should be appreciated that only the sealing element that is closest to the proximal end, but still within the empty space, may be sealed to close off the corresponding empty section of the pouch.

In some instances, the distal end of the surgical pouch is not coupled to a structure so that the distal end of the surgical pouch is positioned above the proximal end. For example, the surgical pouch may be positioned next to the patient—e.g., on the table or bedside next to the patient. In such case, the exposed internal body parts within the pouch may be pushed towards the proximal end of the pouch by the operator. This forms the empty space at the distal end of the pouch, and the operator may then seal any sealing elements that the empty space continues past. In some instances, the operator may lift the distal end of the pouch in addition, or in place of, pushing the exposed internal body parts to the proximal end of the pouch. Lifting the distal end of the pouch displaces the exposed internal body parts towards the proximal end of the pouch, creating empty space at the distal end of the pouch. The operator may then seal any sealing element that the empty space continues past.

Over time, portions of the exposed internal body parts are inserted into the body opening. For example, a physician may slowly and gently press some of the exposed body parts within the body of the patient. In some instances, the exposed internal body parts may be swollen or inflamed, allowing more and more of the exposed internal body parts to be inserted into the body as the swelling and inflammation is reduced over time. As more of the exposed internal body parts are inserted into the body of the patient, more empty space is created at the distal end of the pouch. As the empty space grows and continues past an additional sealing element, the operator may seal off the additional sealing element to close off an empty section of the pouch that has formed when portions of the exposed internal body parts are inserted into the body of the patient. This may continue until all sealing elements have been sealed and the exposed internal body parts completely inserted into the body of the patient.

After the exposed internal body parts are inserted into the body of the patient, the securing element may be removed from the patient. For example, if the securing element comprises a collapsible structure, then the securing element may again be collapsed by the operator and removed out of the opening of the body while collapsed. In other instances, the operator may gently pull the surgical pouch away from the body opening, causing the sealing element to collapse under pressure against the body and to be removed from the body of the patient. In yet other instances, for example where the sealing element includes adhesive used to adhere the opening to the body of the patient, the operator pulls the sealing element from the body of the patient.

FIG. 1 illustrates a perspective view of a device for containing exposed internal body parts during insertion into the body, according to some embodiments. As shown, device 100 includes surgical pouch 110 and sealing elements 115*a* and 115*b*. A distal end 101 and proximal end 102 are shown for reference purposes. Also shown for reference purposes are a longitudinal axis L and a latitudinal axis W.

The surgical pouch is shown as a clear polymeric material, such as plastic or silicone.

Sealing elements 115*a* and 115*b* are shown disposed on the surgical pouch 100 at different positions along the longitudinal axis L. The sealing elements 115*a* and 115*b* are shown as interlocking fasteners that extend across the surgical pouch 110 in the direction of the latitudinal axis W. Sealing element 115*a* is disposed on the pouch 110 closer to the distal end 101 of the device 100 than sealing element 115b. As such, the two sealing elements 115a and 115b sectionalize the surgical pouch 110 into three sections A, B, and C.

Each of the sealing elements 115a and 115b may be sealed to seal off a corresponding section of the surgical pouch 100. For example, sealing element 115a enables section A to be closed off from the remaining portions—sections B and C—of the surgical pouch 110 when the internal body parts are not present in section A. Similarly, sealing element 115b enables section B to be closed off (and ultimately section A as well) from the remaining portion—section C—of the surgical pouch 110 when the internal body parts are not present in sections A and B.

The surgical pouch 110 also includes an opening 120 with a securing element 125 surrounding the opening. The securing element 125 is shown as a ring that is collapsible and resilient in nature. The ring 125 may be collapse to fit within the opening in the body (e.g., abdomen) of a patient. In such case, the ring 125 bends and deforms (e.g., to form a narrow elliptical shape) to enable the ring 125 to enter the opening in the body. The ring 125 may then return to its circular shape once inside the body to secure to the inner wall of the body. Ring 125 may be made from, for example, a polymeric material that is resilient so as to allow the ring 125 to collapse or deform and then return to its uncollapsed or undeformed state.

Device 100 also includes a coupling element 130 that is used to couple the distal end 101 of the device 100 to an external structure (not shown) so that the distal end 101 may hang above the proximal end 102 of the device 100. The coupling element 130 is shown comprising a layer of material that includes a hole 135 which may be used to hang the distal end 101 of the device 100 to the external structure.

Figure 2:
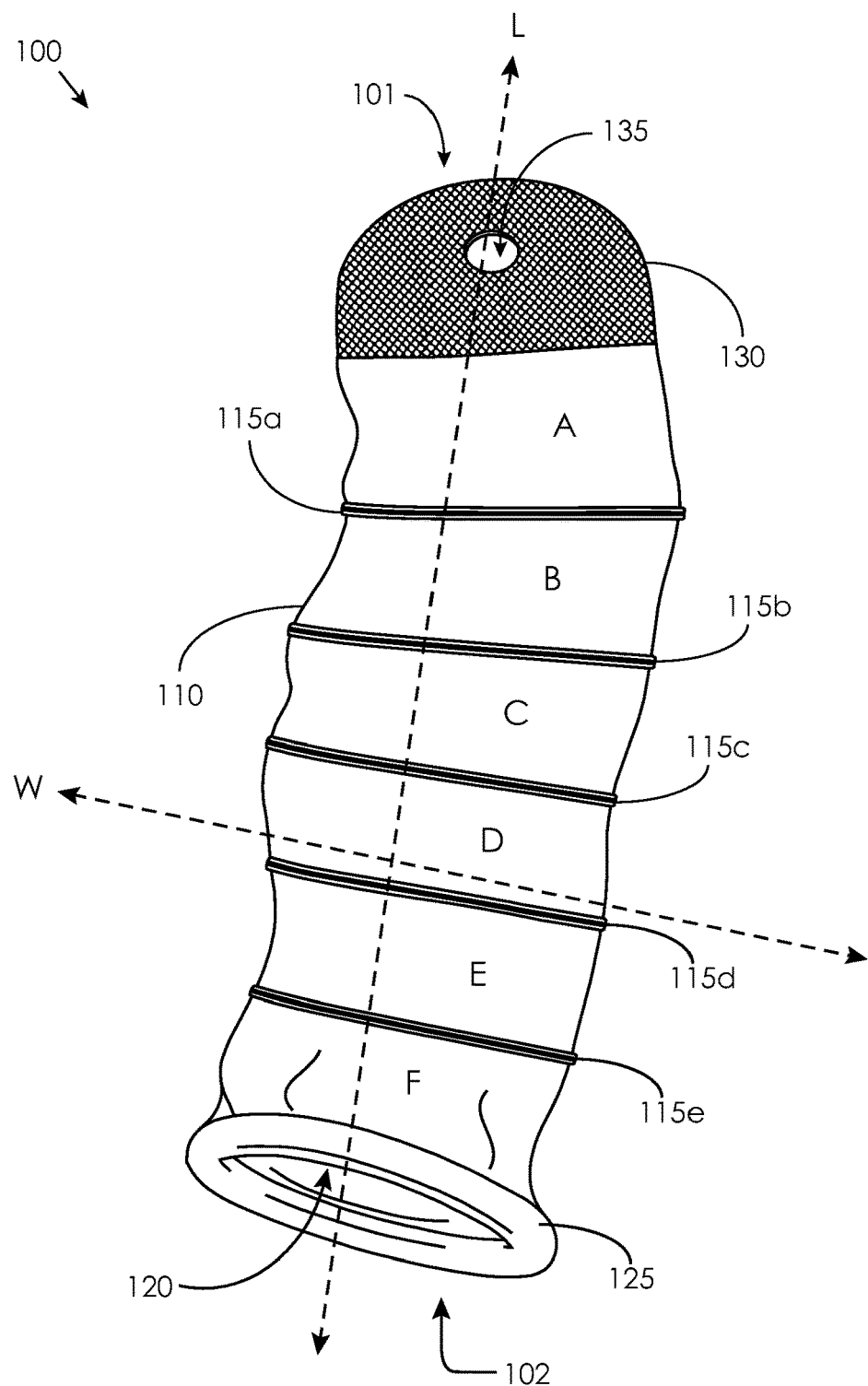
FIG. 2 illustrates a perspective view of a device for containing exposed internal body parts during insertion into the body, according to some embodiments.

FIG. 2 illustrates a perspective view of another exemplary device for containing exposed internal body parts during insertion into the body, according to some embodiments. As shown, device 100 includes surgical pouch 110 and sealing elements 115a, 115b, 115c, 115d, and 115e. A distal end 101 and proximal end 102 are shown for reference purposes. Also shown for reference purposes are a longitudinal axis L and a latitudinal axis W.

Sealing elements 115a, 115b, 115c, 115d, and 115e are shown disposed on the surgical pouch 100 at different positions along the longitudinal axis L. The sealing elements 115a, 115b, 115c, 115d, and 115e are shown as interlocking fasteners that extend across the surgical pouch 110 in the direction of the latitudinal axis W. The sealing elements 115a, 115b, 115c, 115d, and 115e are shown spaced apart with sealing element 115a disposed closest to the distal end 101 of the device 100, and with sealing element 115e disposed closest to the proximal end 102 of the device 100. As such, the sealing elements 115a, 115b, 115c, 115d, and 115e sectionalize the surgical pouch 110 into sections A, B, C, D, E, and F.

Each of the sealing elements 115a, 115b, 115c, 115d, and 115e may be sealed to seal off a corresponding section of the surgical pouch 100. For example, sealing element 115a enables section A to be closed off from the remaining portions—sections B, C, D, E, and F—of the surgical pouch 110 when the internal body parts are not present in section A. Sealing element 115b enables section B to be closed off (and ultimately section A as well) from the remaining portion—sections C, D, E, and F—of the surgical pouch 110 when the internal body parts are not present in sections A and B. Sealing element 115c enables section C to be closed off (and ultimately sections A and B as well) from the remaining portion—sections D, E, and F—of the surgical pouch 110 when the internal body parts are not present in sections A, B, and C. Sealing element 115d enables section D to be closed off (and ultimately sections A, B, and C as well) from the remaining portion—sections E and F—of the surgical pouch 110 when the internal body parts are not present in sections A, B, C, and D. And, similarly, sealing element 115e enables section E to be closed off (and ultimately sections A, B, C, and D as well) from the remaining portion—section F—of the surgical pouch 110 when the internal body parts are not present in sections A, B, C, D, and E. It should be appreciated that e number of sealing elements shown in FIGS. 1 and 2 are exemplary and that the number of sealing elements may vary in other embodiments.

The surgical pouch is shown as a clear polymeric material, such as plastic or silicone. The surgical pouch 110 also includes an opening 120 with a securing element 125 surrounding the opening. The securing element 125 is shown as a ring that is collapsible and resilient in nature. The ring 125 may be collapse to fit within the opening in the body (e.g., abdomen) of a patient. In such case, the ring 125 bends and deforms (e.g., to form a narrow elliptical shape) to enable the ring 125 to enter the opening in the body. The ring 125 may then return to its circular shape once inside the body to secure to the inner wall of the body. Ring 125 may be made from a polymeric material that is resilient so as to allow the ring 125 to collapse or deform and then return to its uncollapsed or undeformed state.

Device 100 also includes a coupling element 130 that is used to couple the distal end 101 of the device 100 to an external structure (not shown) so that the distal end 101 may hang above the proximal end 102 of the device 100. The coupling element 130 is shown comprising a layer of material that includes a hole 135 which may be used to hang the distal end 101 of the device 100 to the external structure.

Figure 3:
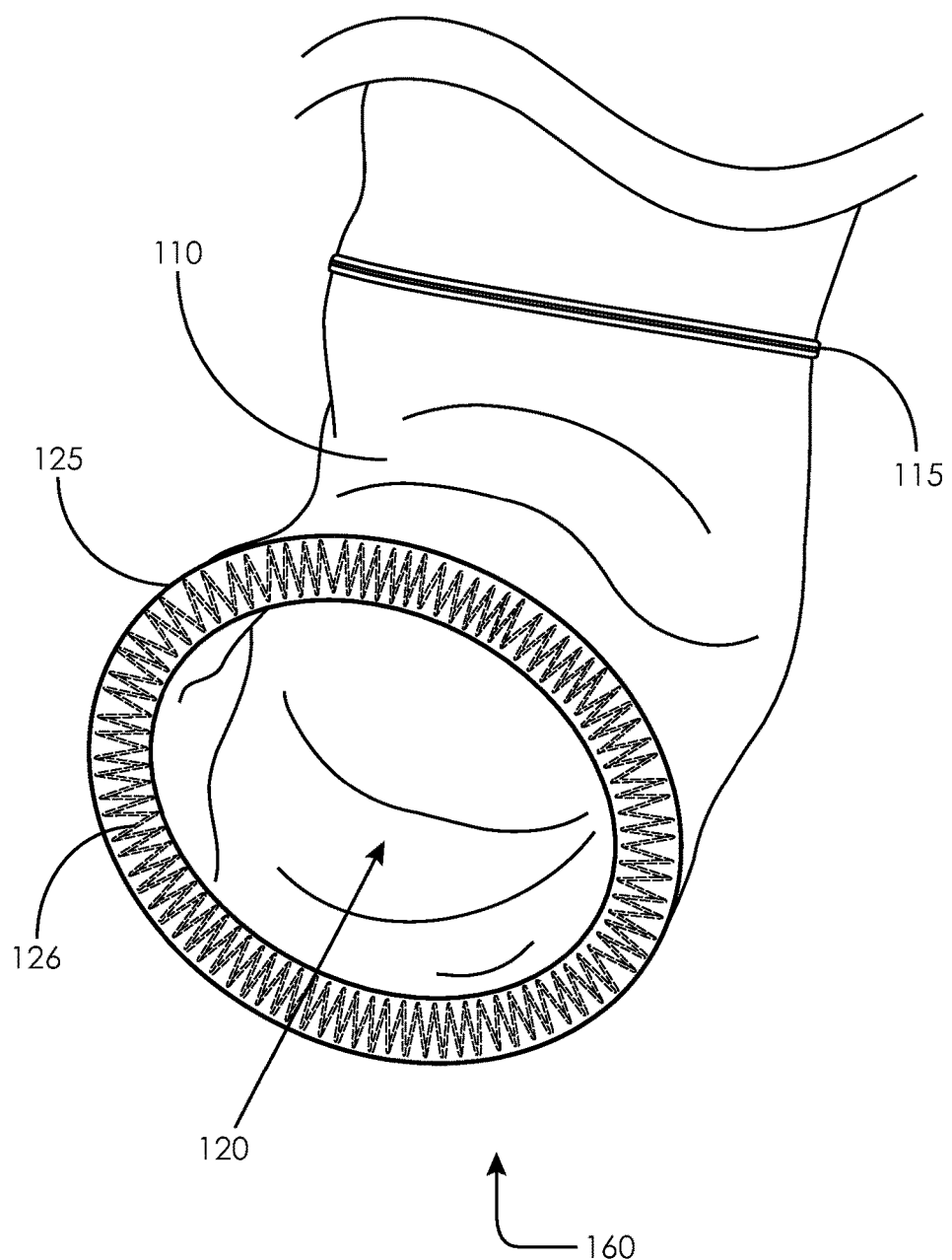
FIG. 3 illustrates a close-up perspective view of a securing element, according to some embodiments.

FIG. 3 illustrates a close-up perspective view of a securing element, according to some embodiments. As shown, securing element 125 comprises a ring disposed around the opening 120 of surgical pouch 110. Sealing element 115 is disposed on surgical pouch 110 distally from the securing element 125. In the embodiment shown, ring 125 includes a spring structure 126 made from a metal or metal alloy, for example. The spring 126 provides ring 125 with the collapsible and resilient properties that facilitate entry into the body opening and securing to inner wall of the body of the patient. The ring 125 is shown enclosed within the polymeric material of the pouch 110 surrounding the opening 120 of the pouch 110. In other embodiments, the securing element 125 may be coupled to the pouch by other means that attach, connect, or otherwise couple the securing element 125 to the pouch 110 near the opening 120.

FIGS. 4-7 illustrate a perspective view of the device shown in FIG. 1 at different times during use, according to some embodiments. Again, distal end 101 and proximal end 102 are shown for reference purposes. As shown in the figures, device 100 includes a surgical pouch 110 having sealing elements 115a and 115b. Sealing elements 115a and 115b are shown as interlocking fasteners. The surgical pouch 110 is shown sectionalized into three sections A, B, and C by sealing elements 115a and 115.

The exposed internal body parts 225 of baby 200 has been inserted within the surgical pouch 110 and contained therein. An opening (not shown) of the surgical pouch 110 is located at the proximal end 102 and inserted within the opening 220 of the abdomen 235 of baby 200. A securing element (such as the one shown in FIG. 3, for example, but not shown in FIGS. 4-7) is disposed around the opening of the surgical pouch 110 and is secured on the inside of the inner wall of the abdomen 235 of the baby 200. At the distal end 101 of the device 100 is a coupling element 130 that includes a hole 135 enabling the distal end 101 of the device 100 to hang from structure 250.

Figure 4:
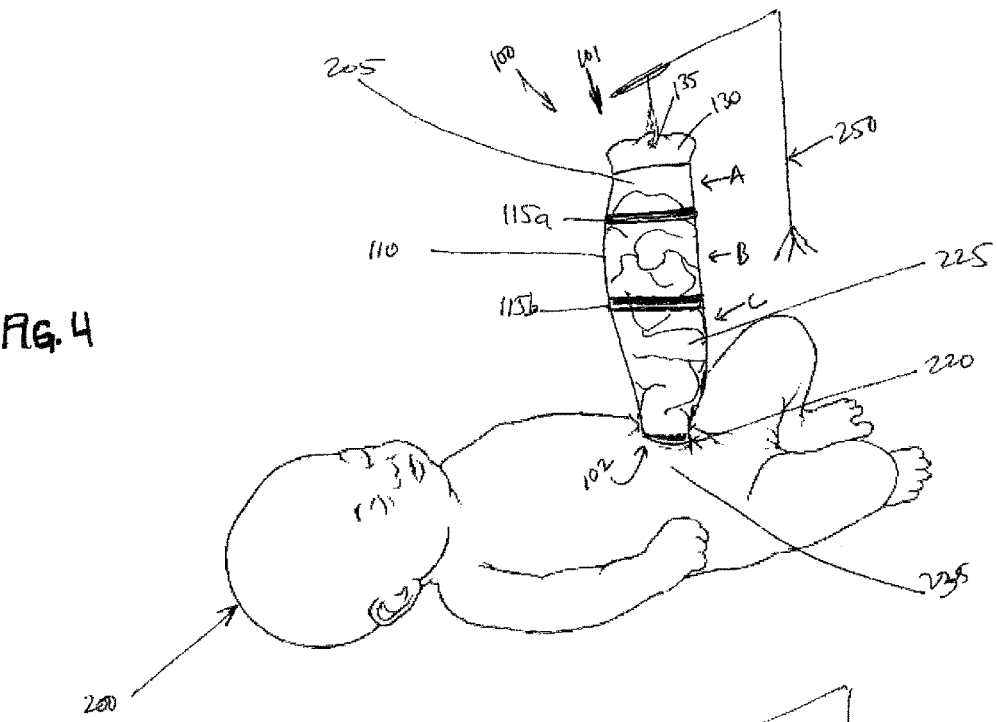
FIG. 4 illustrates a perspective view of the device shown in FIG. 1 containing exposed internal body parts before a sealing element is sealed, according to some embodiments.

FIG. 4 illustrates a perspective view of the device shown in FIG. 1 containing exposed internal body parts 225 before either sealing element 115a or 115b are sealed. As shown, the exposed internal body parts 225 are contained within sections A, B, and C. Thus, both sealing elements 115a and 115b are left unsealed. The internal volume of the surgical pouch includes the exposed internal body parts 225 and empty space 205 at the distal end 101 of the surgical pouch 110.

Figure 5:
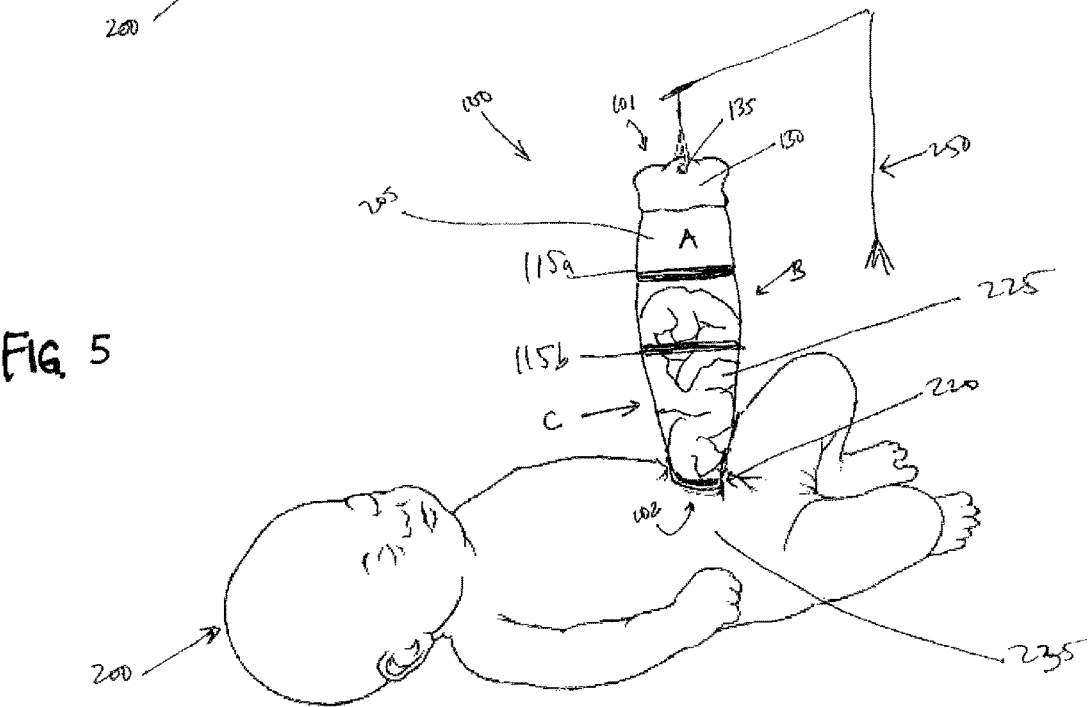
FIG. 5 illustrates a perspective view of the device shown in FIG. 4 after some exposed internal body parts have been inserted within the patient and a first sealing element sealed, according to some embodiments.

FIG. 5 illustrates a perspective view of the device 100 shown in FIG. 4 after some exposed internal body parts 225 have been inserted within the baby 200 and sealing element 115a sealed. As shown, the exposed internal body parts 225 are contained only within sections B and C with empty space 205 in section A and in part of section B. Sealing element 115b is left unsealed and sealing element 115a is sealed to close off the empty space in section A.

FIG. 6 illustrates a perspective view of the device 100 shown in FIG. 4 after some exposed internal body parts 225 have been inserted within baby 200 and sealing element 115b sealed. As shown, the exposed internal body parts 225 are contained only within section C with empty space 205 in sections A and B and in part of section C. Sealing element 115a was previously sealed (e.g., as described in FIG. 4) to close off the empty space in section A, and now sealing element 115b is sealed to close off the empty space 205 in section B.

FIG. 7 illustrates a perspective view of the device 100 shown in FIG. 4 after all of the exposed internal body parts 225 have been inserted within the baby 100. As shown, section C of surgical pouch 110 is now empty since all of the exposed internal body parts 225 have been inserted within the opening 220 in the abdomen 235 of baby 200. The device 100 may now be removed from the baby 200. For example, the securing element (not shown) may be removed from the opening 220 of the baby 200. For example, the securing element comprises a collapsible structure and the securing element may be collapsed by the physician to be removed out of the opening of the body while collapsed. In other instances, the operator may pull the surgical pouch away from the body opening, causing the sealing element to collapse under pressure against the body and to be removed from the body of the patient.

Methods

In some aspects of the present disclosure, methods of containing exposed internal body parts of a human or veterinary patient during insertion into the body of the patient using are provided. In certain embodiments, the methods comprise inserting exposed internal body parts of a patient within a device including a surgical pouch and one or more sealing elements disposed on the surgical pouch. The methods also comprise displacing the exposed internal body parts toward the proximal end of the pouch and past a sealing element, such that the exposed internal body parts are proximally located to the sealing element. For example, portions of the exposed internal body parts of the patient are inserted within the body of a patient (e.g., the abdomen of a baby) and the internal body parts displaced towards the proximal end of the pouch. The methods also include sealing the sealing element disposed on the pouch when the exposed internal body parts are displaced past the sealing element, wherein an empty section of the pouch is closed off when the sealing element is sealed. In some embodiments, more than one sealing element is present and each sealing element may be sealed as the body parts are displaced past each sealing element.

The methods also comprise securing the surgical pouch to the patient using a securing element disposed on the device. In some instances, the proximal end of the surgical pouch may include a sealing element that is a collapsible structure that may be collapsed by the operator and inserted into the opening in the body of the patient. Once inside, the collapsible structure returns to its uncollapsed state and secures behind the internal wall of the body. In other embodiments, the opening may include adhesive sealing elements which enable the opening to be adhered to the body of the patient around the opening in the body.

In some instances, the distal end of the surgical pouch is raised up above the body opening. The surgical pouch may include, for example, a coupling element that couples the distal end of the surgical pouch to an external structure so that the distal end of the surgical pouch may be positioned above the proximal end. In such instances, gravity assists to displace the exposed internal body parts at the proximal end of the surgical pouch end—i.e., towards the opening of the surgical pouch.

In some instances, the exposed internal body parts do not fill the entire internal volume of the surgical pouch. As a result, the distal end of a surgical pouch may include empty space. If the empty space at the distal end of the surgical pouch continues past a sealing element, then that sealing element may be sealed to close off the empty section of the internal volume of the pouch. For example, the operator may slide an interlocking fastener to close off the empty section of the internal volume of the pouch. If more than one sealing element is implemented and the empty space continues past multiple sealing elements, then each, or any one, of those sealing elements may be sealed. It should be appreciated that only sealing the sealing element that is closest to the proximal end, but within the empty space, enables the remaining empty sections to be closed off as well.

In some instances, the distal end of the surgical pouch is not coupled to structure so that the distal end of the surgical pouch is positioned above the proximal end. For example, the surgical pouch may be positioned next to the patient—e.g., on the table or bedside next to the patient. In such case, the exposed internal body parts within the pouch may be pushed towards the proximal end of the pouch by the operator. This forms the empty space at the distal end of the pouch, and the operator may then seal any sealing elements that the empty space continues past. In some instances, the operator may lift the distal end of the pouch in addition, or in place of, pushing the exposed internal body parts to the proximal end of the pouch. Lifting the distal end of the pouch displaces the exposed internal body parts towards the proximal end of the pouch, creating empty space at the distal end of the pouch. The operator may then seal any sealing elements that the empty space continues past.

Over time, portions of the exposed internal body parts are inserted into the body opening. For example, a physician may slowly press some of the exposed body parts within the body of the patient. In some instances, the exposed internal body parts may be swollen or inflamed, allowing more and more of the exposed internal body parts to be inserted into the body as the swelling and inflammation is reduced over time. As more of the exposed internal body parts are inserted into the body of the patient, more empty space is created at the distal end of the pouch. As the empty space grows and continues past an additional sealing element, the operator may seal the additional sealing element to close off the additional empty sections that has formed from portions of the exposed internal body parts being inserted into the body of the patient. This may continue until all sealing elements have been sealed and the exposed internal body parts completely inserted into the body of the patient.

After the exposed internal body parts are inserted into the body of the patient, the securing element may be removed from the patient. For example, if the securing element comprises a collapsible structure, then the securing element may again be collapsed by the operator and removed out of the opening of the body while collapsed. In other instances, the operator may gently pull the surgical pouch away from the body opening, causing the sealing element to collapse under pressure against the body and to be removed from the body of the patient. In yet other instances, for example where the sealing element includes adhesive used to adhere the opening to the body of the patient, the operator pulls the sealing element from the body of the patient.

Utility

The subject devices and methods find use in a variety of different applications where internal body parts are exposed out of an opening in the body of a patient. In certain embodiments, the devices and methods are directed to containing exposed internal body parts of a newborn baby during insertion of the exposed internal body parts into the body of the baby.

Containing the exposed internal body parts with the subject devices and methods enable the exposed internal body parts to be shielded from trauma, infection, and dehydration until the body parts are put back within the body. Often the exposed internal body parts may be swollen and inflamed and require time before the swelling and inflammation subside to permit the internal body parts to be safely put back within the body.

As described above, the method may include inserting exposed internal body parts of a patient within a device including a surgical pouch and one or more sealing elements disposed on the surgical pouch; and displacing the exposed internal body parts toward the proximal end of the pouch and past a sealing element, such that the exposed internal body parts are proximally located to the sealing element. For example, portions of the exposed internal body parts of the patient are inserted within the body of a patient (e.g., the abdomen of a baby) and the internal body parts displaced towards the proximal end of the pouch. The methods also include sealing the sealing element disposed on the pouch when the exposed internal body parts are displaced past the sealing element, wherein an empty section of the pouch is closed off when the sealing element is sealed. In some embodiments, more than one sealing element is present and each sealing element may be sealed as the body parts are displaced past each sealing element.

The subject devices and methods may enable a single operator to more easily close off the empty section of the surgical pouch without the assistance of another person. Furthermore, the sealing elements are easily sealed and eliminate the cumbersome cinching and tying of the surgical pouch. Moreover, sealing elements such as interlocking fasteners ensures a "good" seal when sealed and are also well maintained thereafter.

Kits

Also provided are kits for use in practicing the subject methods, where the kits may include one or more of the devices described above. In some instances, the kits may include multiple devices with a different number of sealing elements disposed on the device. In some instances, the kits may include multiple devices with different sized devices. In some instances, the kits may also include a structure for hanging the device above the opening in the body of the patient. In some instances, the kits may include products used to sterilize or otherwise clean the body of the patient. Various components may be packaged as desired, e.g., together or separately.

In addition to above mentioned components, the subject kits typically further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Although the foregoing embodiments have been described in some detail by way of illustration and example for purposes of clarity of understanding, it is readily apparent to those of ordinary skill in the art in light of the teachings of the present disclosure that certain changes and modifications may be made thereto without departing from the spirit or scope of the appended claims. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein.

The invention claimed is:

1. A device for containing exposed internal body parts during insertion into the body of a human or veterinary patient, the device comprising:
    a surgical pouch adapted to contain exposed internal body parts of a patient that are extending outside an opening in a body of the patient, the pouch comprising:
        a proximal end; and
        a distal end, the proximal end including an opening in the pouch adapted to fit within the opening in the body; and
    a first interlocking fastener that does not provide an airtight seal and is integrated with the pouch and is disposed on an internal surface of the pouch between the distal end and the proximal end of the surgical pouch and extends along an entire width of the pouch in a latitudinal direction, such that a first section of the pouch is closed off when the first interlocking fastener is closed;
    at least two additional interlocking fasteners that do not provide an airtight seal and are integrated with the pouch and are disposed on an internal surface of the pouch between the first interlocking fastener and the proximal end of the pouch and extend along the entire width of the pouch in a latitudinal direction, wherein the at least two additional interlocking fasteners are disposed at different distances from the proximal end, wherein the interlocking fasteners are spaced a set distance apart from each other, wherein the set distance is the same.

2. The device of claim 1, comprising a securing element for securing the opening of the pouch to the opening in the body of the patient.

3. The device of claim 2, wherein the securing element comprises a ring positioned around a perimeter of the opening of the pouch, wherein the ring is collapsible for insertion in the opening of the body, and wherein the ring is resilient such that the ring is adapted to return to an uncollapsed state when inserted into the opening in the body of the patient.

4. The device of claim 3, wherein the ring includes a spring.

5. The device of claim 2, comprising a coupling element disposed at the distal end of the pouch, the coupling element for hanging the distal end of the pouch above the proximal end of the pouch.

6. The device of claim 1, comprising a coupling element disposed at the distal end of the pouch, the coupling element for hanging the distal end of the pouch above the proximal end of the pouch.

7. A method for containing exposed internal body parts of a human or veterinary patient during insertion into the body of the patient, the method comprising:
    inserting exposed internal body parts of a patient within a device according to claim 1;
    displacing the exposed internal body parts toward the proximal end of the pouch and past the first interlocking fastener to a first position, the first position between the first interlocking fastener and the proximal end of the pouch; and
    closing the first interlocking fastener disposed on the pouch when the exposed internal body parts are displaced to the first position, wherein the first section of the pouch is closed off when the first interlocking fastener is closed.

8. The method of claim 7, comprising:
    displacing the exposed internal body parts toward the proximal end of the pouch and past a second interlocking fastener to a second position, wherein the second interlocking fastener does not provide an airtight seal and is integrated with the pouch and is disposed on an internal surface of the pouch between the first interlocking fastener and the proximal end of the pouch and extends along the entire width of the pouch in a latitudinal direction, and wherein the second position is between the second interlocking fastener and the proximal end of the pouch; and
    closing the second interlocking fastener when the exposed internal body parts are displaced to the second position, wherein a second section of the pouch is closed off when the second interlocking fastener is closed.

9. The method of claim 8, comprising:
    displacing the exposed internal body parts toward the proximal end of the pouch and past a third interlocking fastener to a third position, wherein the third interlocking fastener does not provide an airtight seal and is integrated with the pouch and is disposed on an internal surface of the pouch between the second interlocking fastener and the proximal end of the pouch and extends along the entire width of the pouch in a latitudinal direction, and wherein the third position is between the third interlocking fastener and the proximal end of the pouch; and
    closing the third interlocking fastener when the exposed internal body parts are displaced to the third position, wherein a third section of the pouch is closed off when the third interlocking fastener is closed.

10. The method according to claim 8, wherein each of the interlocking fasteners comprises snap fit elements or hook and loop elements.

11. The method of claim 7, comprising securing the opening of the pouch to the opening in the body of the patient using a securing element on the device.

12. The method of claim 11, wherein the securing element comprises a collapsible and resilient ring positioned around a perimeter of the opening of the pouch, and wherein securing the opening of the pouch to the opening in the body of the patient comprises:
collapsing the ring;
inserting the collapsed ring into the opening of the body; and
returning the collapsed ring to an uncollapsed state to secure the uncollapsed ring to an inner wall of the body of the patient.

13. The method of claim 12, wherein the ring includes a spring.

14. The method of claim 12, comprising:
collapsing the ring again when all of the exposed internal body parts are inserted into the body of the patient; and
removing the collapsed ring out of the opening of the body of the patient.

15. The method of claim 14, comprising coupling a coupling element disposed at the distal end of the pouch to an external structure such that the distal end of the pouch hangs above the proximal end of the pouch.

16. The method of claim 7, comprising coupling a coupling element disposed at the distal end of the pouch to an external structure such that the distal end of the pouch hangs above the proximal end of the pouch.

17. The method of claim 7, wherein the patient is a baby and the exposed internal body parts comprise an intestine.

18. The device according to claim 1, wherein at least one of the interlocking fasteners comprises snap fit elements or hook and loop elements.

19. The device according to claim 1, wherein at least one of the interlocking fastener fasteners comprises a sliding clasp.

20. The device according to claim 1, wherein each of the interlocking fasteners comprises snap fit elements or hook and loop elements.

21. The device according to claim 1, wherein the surgical pouch further comprises a seam.

22. The device according to claim 21, wherein the seam is located along two sides of the surgical pouch along a longitudinal axis, such that the seam extends from the proximal end of the device to the distal end of the device.

23. The device according to claim 1, wherein the first interlocking fastener is positioned in proximity to the distal end of the surgical pouch and sectionalizes the distal end from the proximal end of the surgical pouch when the first interlocking fastener is closed.

24. A device for containing exposed internal body parts during insertion into the body of a human or veterinary patient, the device comprising:
a surgical pouch adapted to contain exposed internal body parts of a patient that are extending outside an opening in a body of the patient, the pouch comprising:
a proximal end; and
a distal end, the proximal end including an opening in the pouch adapted to fit within the opening in the body;
a first interlocking fastener that is integrated with the pouch and is disposed on an internal surface of the pouch between the distal end and the proximal end of the surgical pouch and extends along an entire width of the pouch in a latitudinal direction, such that a first section of the pouch is closed off when the first interlocking fastener is closed;
a second interlocking fastener that is integrated with the pouch and is disposed on an internal surface of the pouch between the first interlocking fastener and the proximal end of the surgical pouch and extends along the entire width of the pouch in a latitudinal direction, such that a second section of the pouch is closed off when the second interlocking fastener is closed;
a third interlocking fastener that is integrated with the pouch and is disposed on an internal surface of the pouch between the second interlocking fastener and the proximal end of the surgical pouch and extends along the entire width of the pouch in a latitudinal direction, such that a third section of the pouch is closed off when the third interlocking fastener is closed;
a fourth interlocking fastener that is integrated with the pouch and is disposed on an internal surface of the pouch between the third interlocking fastener and the proximal end of the surgical pouch and extends along the entire width of the pouch in a latitudinal direction, such that a fourth section of the pouch is closed off when the fourth interlocking fastener is closed, wherein the first interlocking fastener, second interlocking fastener, third-interlocking fastener and fourth interlocking fastener do not provide an airtight seal,
wherein the interlocking fasteners are spaced a set distance apart from each other, wherein the set distance is the same;
a securing element for securing the opening of the pouch to the opening in the body of the patient, wherein the securing element comprises a ring positioned around a perimeter of the opening of the pouch, wherein the ring is collapsible for insertion in the opening of the body, and wherein the ring is resilient such that the ring is adapted to return to an uncollapsed state when inserted into the opening in the body of the patient; and
a coupling element disposed at the distal end of the pouch, the coupling element for hanging the distal end of the pouch above the proximal end of the pouch.

25. The device of claim 24, comprising a fifth interlocking fastener that is integrated with the pouch and is disposed on an internal surface of the pouch between the fourth interlocking fastener and the proximal end of the surgical pouch and extends along the entire width of the pouch in a latitudinal direction, such that a fifth section of the pouch is closed off when the fifth interlocking fastener is closed, wherein the fifth interlocking fastener does not provide an airtight seal.

26. The device according to claim 25, wherein each of the interlocking fasteners comprises snap fit elements or hook and loop elements.

27. The device according to claim 24, wherein each of the interlocking fasteners comprises snap fit elements or hook and loop elements.

* * * * *